(12) United States Patent
Yu et al.

(10) Patent No.: US 8,070,815 B2
(45) Date of Patent: Dec. 6, 2011

(54) V-SHAPED STAPLE FOR SPINAL PROSTHESIS

(75) Inventors: Kidong Yu, Memphis, TN (US); Mark Dace, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 640 days.

(21) Appl. No.: 12/187,125

(22) Filed: Aug. 6, 2008

(65) Prior Publication Data

US 2010/0036496 A1    Feb. 11, 2010

(51) Int. Cl.
*A61F 2/44* (2006.01)

(52) U.S. Cl. .................. 623/17.14; 623/17.11

(58) Field of Classification Search .... 623/17.11–17.16, 623/237; 606/75, 280, 293; *A61B 17/56*
See application file for complete search history.

(56) References Cited

U.S. PATENT DOCUMENTS

| 6,096,080 A | * | 8/2000 | Nicholson et al. | 623/17.16 |
| 2005/0149189 A1 | * | 7/2005 | Mokhtar et al. | 623/17.11 |
| 2008/0051897 A1 | * | 2/2008 | Lopez et al. | 623/17.13 |
| 2008/0051900 A1 | * | 2/2008 | de Villiers et al. | 623/17.16 |

OTHER PUBLICATIONS

U.S. Appl. No. 11/757,084, filed Jun. 2007, Carls et al.*

* cited by examiner

*Primary Examiner* — Eduardo C Robert
*Assistant Examiner* — James Palmer (57) ABSTRACT

An intervertebral implant system for positioning between an upper vertebra and a lower vertebra is provided. The implant system comprises an intervertebral implant and a staple. The implant comprises an inferior plate and a superior plate, while the superior plate has a vertebral surface facing the upper vertebra and the inferior plate has a vertebral surface facing the lower vertebra. There are two grooves on at least one vertebral surface extending at an angle outward from a centerline on the vertebral surface as they extend from the anterior portion of the plate toward the posterior portion of the plate. When in use, the staple is associated with the two grooves for maintaining stability of the intervertebral implant and preventing backing out of the intervertebral implant. The staple also has two arms and has a generally rectangular shape prior to use.

20 Claims, 11 Drawing Sheets

V-SHAPED STAPLE FOR SPINAL PROSTHESIS

TECHNICAL FIELD

The present invention relates generally to intervertebral implants and more particularly, to providing stability to such spinal implants when they are inserted between vertebrae to replace vertebral discs.

BACKGROUND

The human spine is a biomechanical structure with thirty-three vertebral members, and is responsible for protecting the spinal cord, nerve roots and internal organs of the thorax and abdomen. The spine also provides structural support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition. Similarly, neck pain may occur in related ways, i.e., from injury, aging or disease.

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

It is known that intervertebral discs are prone to injury and degeneration. For example, herniated discs are common, and typically occur when normal wear, or exceptional strain, causes a disc to rupture. Degenerative disc disease typically results from the normal aging process, in which the tissue gradually looses its natural water and elasticity, causing the degenerated disc to shrink and possibly to rupture. These conditions often are treated with the use of intervertebral implants.

In particular, areas of the cervical spine and the lumbar spine are particularly prone to the need for intervertebral implants, or artificial disc implants because they are areas where the spine is particularly dynamic. Thus, the implants that are used often are dynamic or motion-preserving implants. There are challenges, however, with dynamic implants and when there are problems, comes poor performance. For example, maintaining the stability of dynamic implants in the disc space, or merely preventing such dynamic implants from backing-out of the disc space after they are surgically inserted are some such challenges.

There, therefore, is a need to increase the stability of dynamic implants in the disc space and also a need to prevent backing-out of such devices after they have been implanted. Further, there is a need to do so without the use of anchors or flanges on the disc and the need for extra preparation of the endplates of the vertebrae for such extra features.

SUMMARY

An intervertebral implant system for positioning between an upper vertebra and a lower vertebra is provided. The implant system comprises an intervertebral implant and a staple. The implant comprises an inferior plate and a superior plate, while the superior plate has a vertebral surface facing the upper vertebra and the inferior plate has a vertebral surface facing the lower vertebra. There are two grooves on at least one vertebral surface extending at an angle outward from a centerline on the vertebral surface as they extend from the anterior portion of the plate toward the posterior portion of the plate. When in use, the staple is associated with the two grooves for maintaining stability of the intervertebral implant and preventing backing out of the intervertebral implant. The staple also has two arms and has a generally rectangular shape prior to use.

The end of each arm of the staple is pointed. In some versions, the grooves are wider at the anterior portion of the plate than at the posterior portion of the plate. Also, the implant further comprises a stop situated on the anterior side of at least one of the plates such that the at least one plate does not move too far into the disc space. The implant further comprises a screw for fastening the staple into the at least one plate to which the staple is inserted. In some versions, the intervertebral implant system further comprises a second staple for fastening the staple into the other of the superior or inferior plate such that both the superior and inferior plates each have a single staple helping to maintain stability of the intervertebral implant and to prevent backing out of the intervertebral implant. With the intervertebral implant system of the present invention, it is preferred that the two grooves on the at least one vertebral surface extend at an angle outward from the centerline on the vertebral surface in the range of 10 degrees to 15 degrees from the anterior portion of the plate toward the posterior portion of the plate.

A different embodiment of the intervertebral implant system of the present invention comprises an intervertebral implant as described above and a staple, wherein the staple has a left half and a right half. Other than this difference, the characteristics of this embodiment are similar to that of aforementioned embodiments, i.e., for example, the shape of the staple, having stops, pointed ends and angles of the arms of the staple.

Additional aspects and features of the present disclosure will be apparent from the detailed description and claims as set forth below.

DETAILED DESCRIPTION

For the purpose of promoting an understanding of the principles of the present disclosure, reference is made to the specific embodiments illustrated in the drawings, and specific language is used to describe the embodiments. It is nevertheless understood that no limitation of the scope of the present disclosure is intended. Any alterations and further modifications of the described embodiments, and any further applications of the principles of the present disclosure as described herein, are fully contemplated, as would occur to one skilled in the art to which the invention relates.

As mentioned above, there is a need to increase the stability of dynamic implants in the disc space and also prevent backing-out of such devices after they have been implanted. Moreover, there is a need to do so without the use of anchors or flanges on the disc and the need for extra preparation of the endplates of the vertebrae for such extra features.

Figure 1:
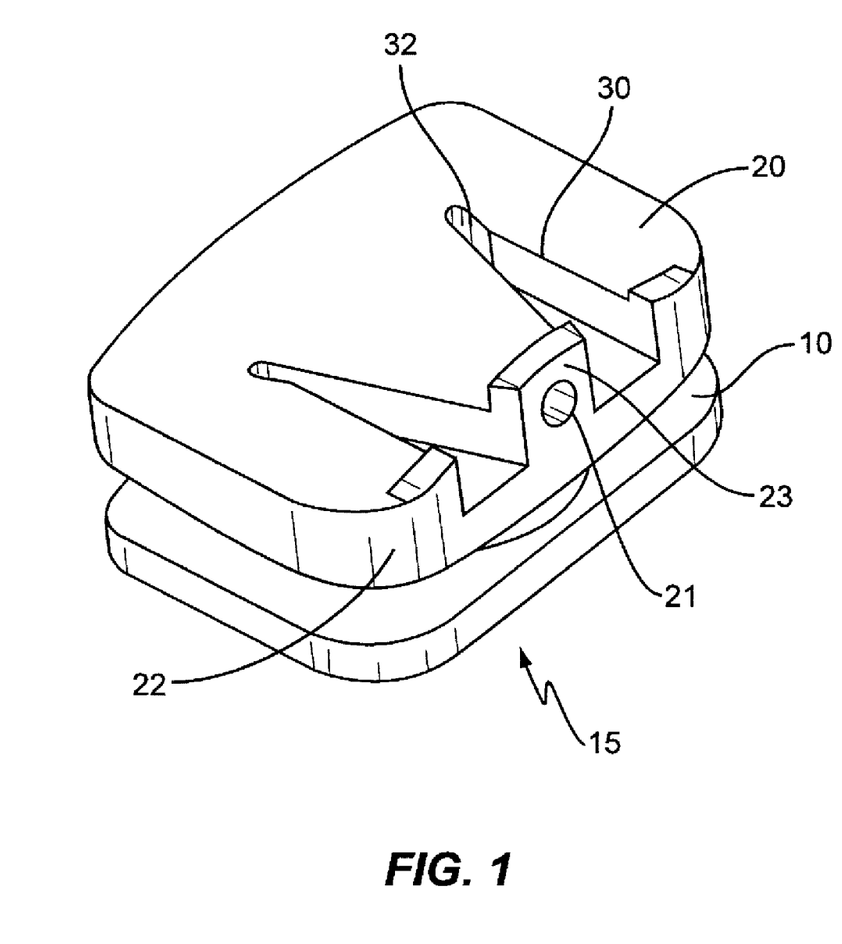
FIG. 1 shows a top isometric view of a spinal implant of the present invention.

FIG. 1 shows a top isometric view of an artificial disc or spinal implant 15 of the present invention. In particular, FIG. 1 shows a superior plate 20 and an inferior plate 10, which cooperate together with articulating surfaces. Shown on the superior plate 20, however, are grooves 30 and 32. At the anterior portion 22 of the plate 20, the groove 30 is relatively wide and it narrows as it extends toward posterior portion of the disc 15 or plate 20. Thus, at the posterior portion of the plate 20, the groove is labeled 32 as it is relatively narrow. Also shown in FIG. 1 is a stop 23, which will be discussed below. Located in or around the stop 23 is a hole 21, which also will be discussed below.

Figure 2:
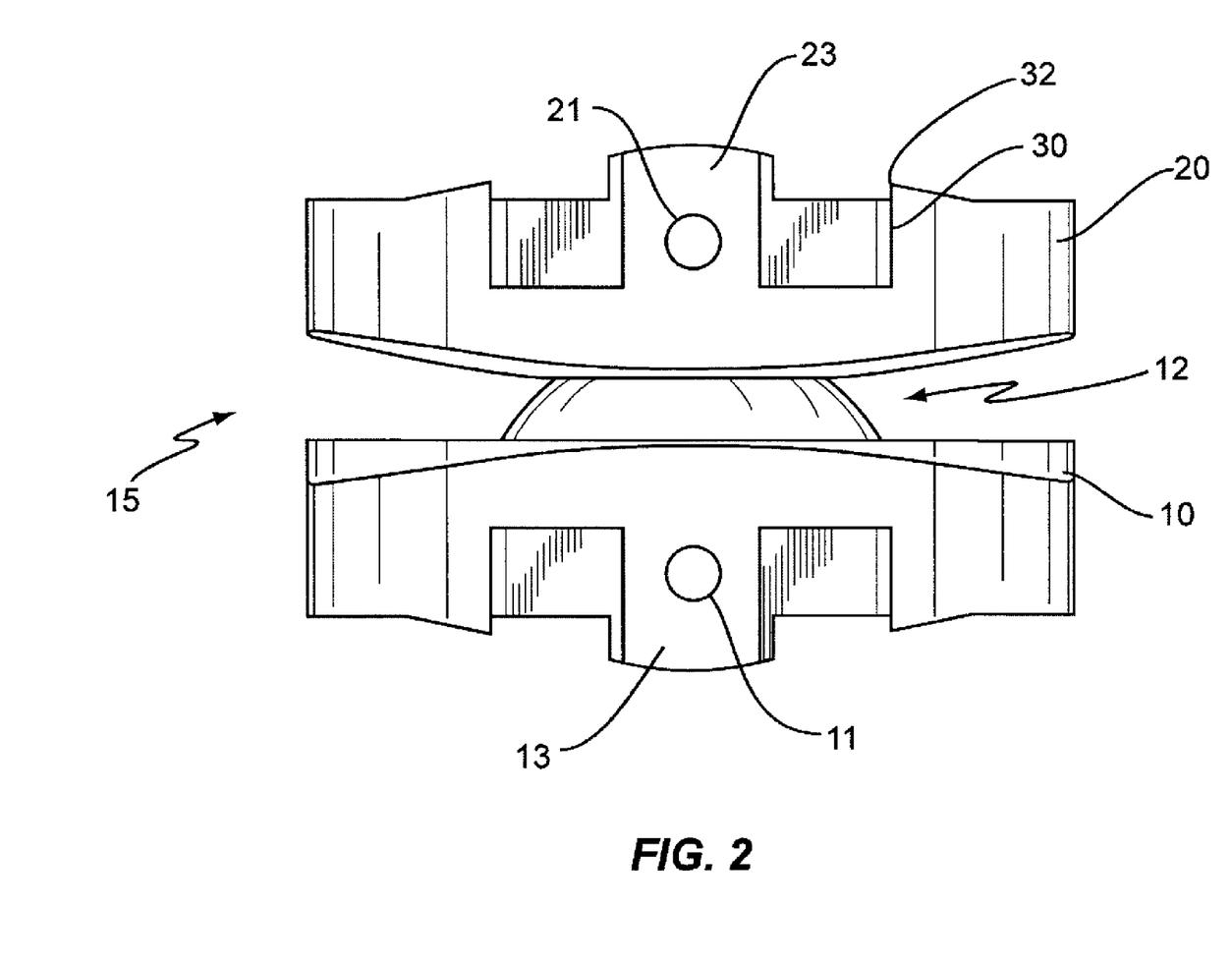
FIG. 2 shows a front view of the spinal implant of FIG. 1.

FIG. 2 shows a front view of the spinal implant 15 of FIG. 1. In particular, FIG. 2 shows a ball-and-socket or ball-and-trough type mechanism 12 of the spinal implant 15, which allows the plates or plates 10 and 20 to articulate, which thereby allows the adjacent vertebrae to which they have been affixed to have motion after the artificial disc 15 is implanted. Located in or around stops 23 and 13, are holes 21 and 13, respectively, which will be discussed below.

Figure 3:
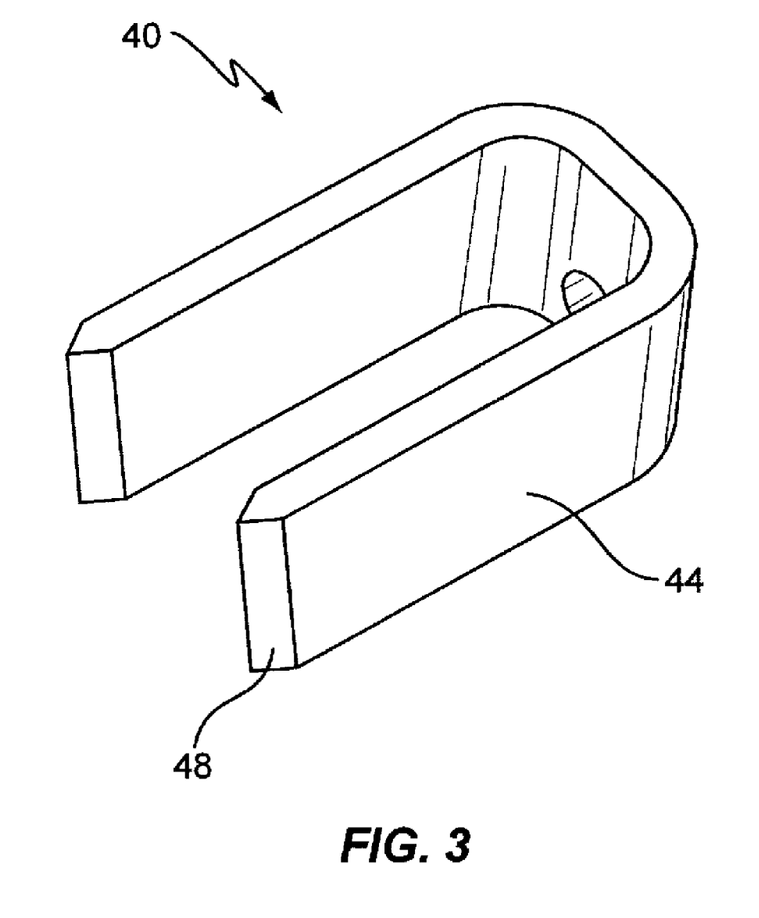
FIG. 3 shows an isometric view of the first or third embodiments of the V-shaped staple of the present invention.

FIG. 3 shows a V-shaped staple 40, which is part of the first embodiment of the present invention. The V-shaped staple 40 comprises two arms 44, and each arm 44 has an end 48 which is pointed (or sharp) for penetrating the endplate of each vertebrae to which the plates 10 or 20 are being affixed. The overall shape of the staple 44 before use can be described as generally rectangular. V-shaped staples of the present invention may be made from materials including titanium, titanium alloys such as nickel-titanium, stainless steel and cobalt chromium, PEEK, PEEK-carbon composites and/or any combination of the above.

Figure 4A:
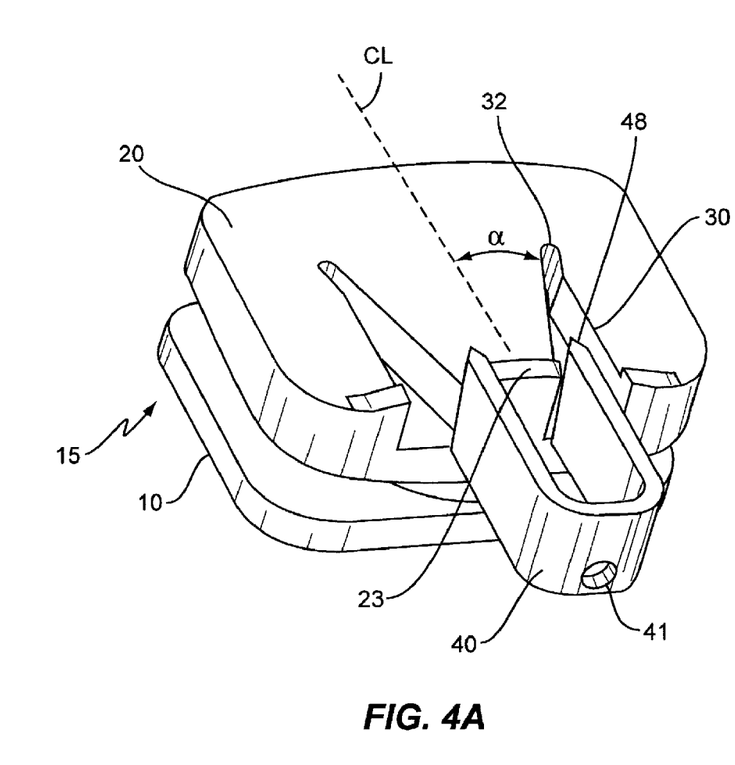
FIGS. 4A and 4B shows isometric views of the procedure for implanting the first embodiment of the V-shaped staple of the present invention.
Figure 4B:
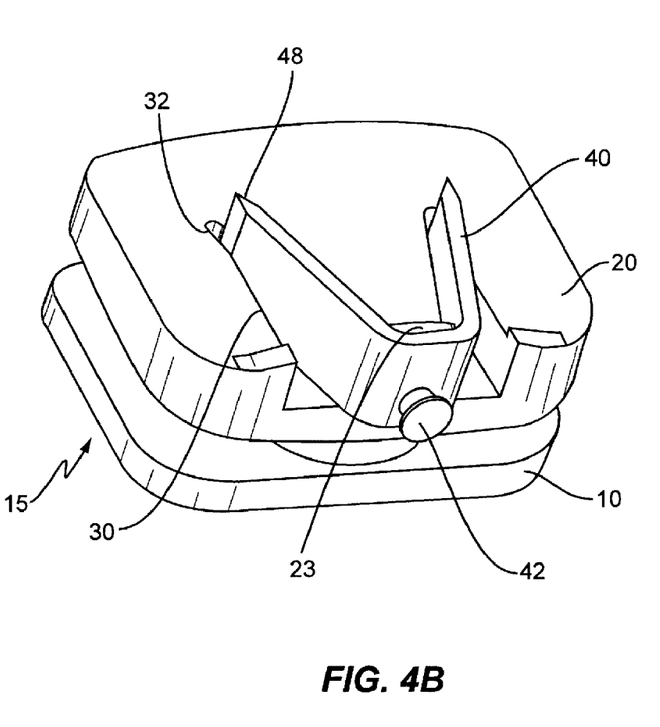

In isometric views, FIGS. 4A and 4B demonstrate the procedure, and specifically the beginning and end stages, for implanting the V-shaped staple 40 into the superior plate 20 of the spinal implant 15 of the present invention. In FIG. 4A, the V-shaped staple 40 is introduced to the implant 15 and the vertebra (not shown). The V-shaped staple 40 can simply be hammered or power-driven through the vertebra that lies above the superior plate 20, while the V-shaped staple 40 moves through the grooves 30 and 32. That is, because of the material of the V-shaped staple 40 and the shape of the groove 30, the V-shaped staple 40 will yield to the groove 30 and change shape from a generally rectangular shape of FIG. 3 to the V-shaped staple of FIGS. 4B. That is, the angle α of each arm 44 of the V-shaped staple 40 from centerline CL (which also can be described as an angle outward from the centerline it moves from the anterior portion to posterior) is in the range of ½ degree to 15 degrees. Such an angle will both allow for the V-shaped staple 40 to enter the vertebrae and groove 30, and also allow for the staple 40 to achieve the purpose of the invention, which is to provide stability to the spinal implant, particularly transverse stability, while also preventing backing out of the implant. Further, note that the relatively narrow grooves 32 toward the posterior end of the plate 20 work to fix or lock the staple 40 in the final position. Also note that for the second embodiment of the V-shaped staple of the present invention, a different range of angle α, is preferred.

FIG. 4B also shows the stop 23 on the superior plate 20. The stop 23 helps prevent the V-shaped staple 40 from causing the plate 20 from moving too far into the disc space. After the V-shaped staple 40 is fully inserted into place, a screw 42 is inserted through hole 41 in staple 40 and into stop 23 and/or partially or directly into plate 20, i.e., depending on the location of hole 41. Specifically, screw 42 maintains stability between the V-shaped staple 40 and each respective plate 10 or 20 of the spinal implant 15. Note that this present procedure and spinal implant 15 is described with reference to the superior plate 20 for illustrative purposes only. That is, it is preferred that a V-shaped staple (in any embodiment described herein) is used on both the superior and inferior plates 20 and 10, respectively, for maximum stability and results, e.g., to prevent backing out.

Figure 5:
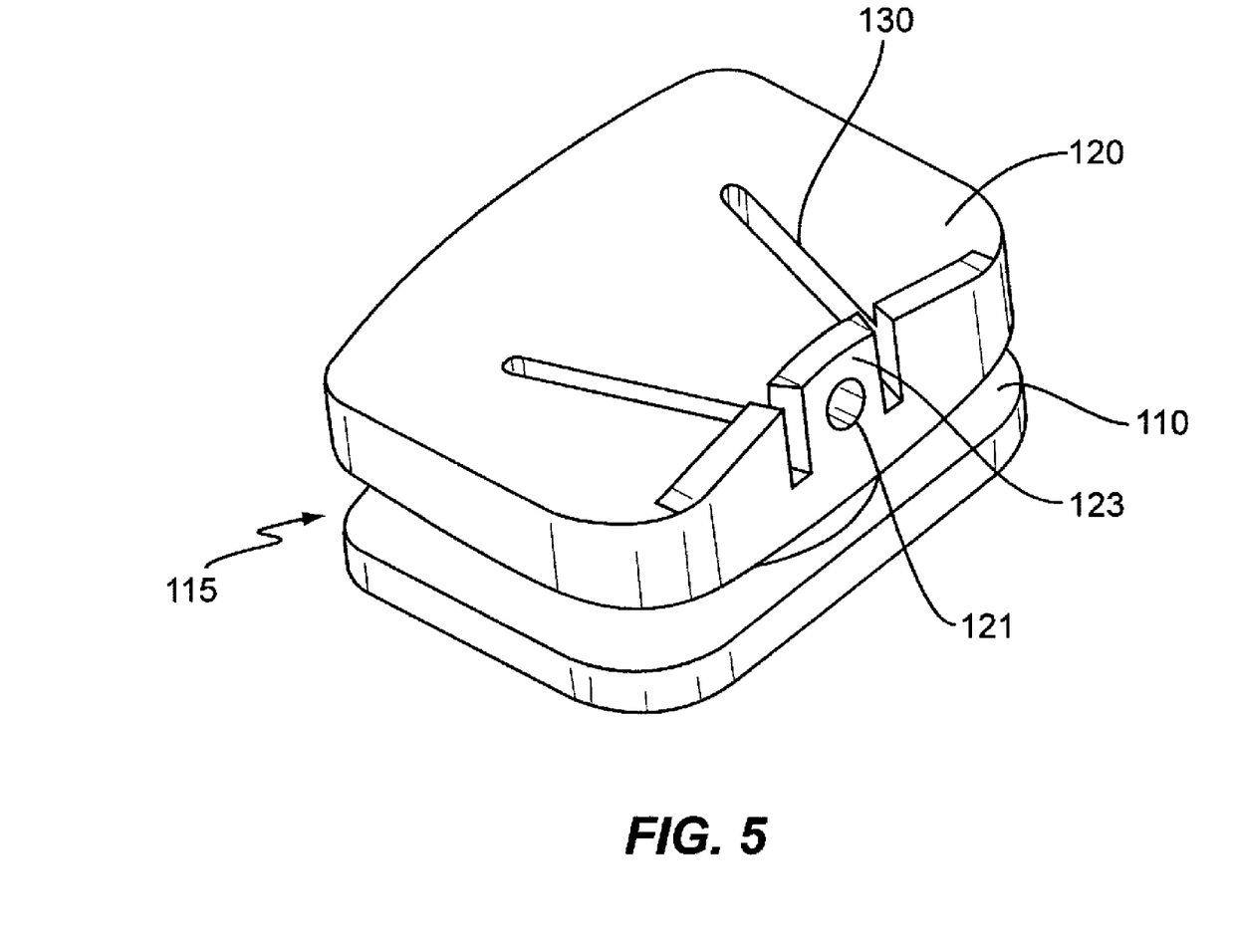
FIG. 5 shows an isometric view of the second embodiment of a spinal implant of the present invention.

FIG. 5 shows an isometric view of a second embodiment of a spinal implant 115 of the present invention. In particular, FIG. 5 shows a superior plate 120 and an inferior plate 110, which cooperate together with articulating surfaces such as a ball-and-socket mechanism of FIG. 2. Shown on the superior plate 20, and as opposed to the embodiment 15 of FIG. 1, the grooves 130 are relatively narrow and of the same width throughout their length. Similar to the embodiment 15, however, implant 115 also contains a stop 123 on its superior plate 120. Located in or around the stop 123 is a hole 121 for a screw 142 (shown in FIG. 6B) to be inserted.

Figure 6A:
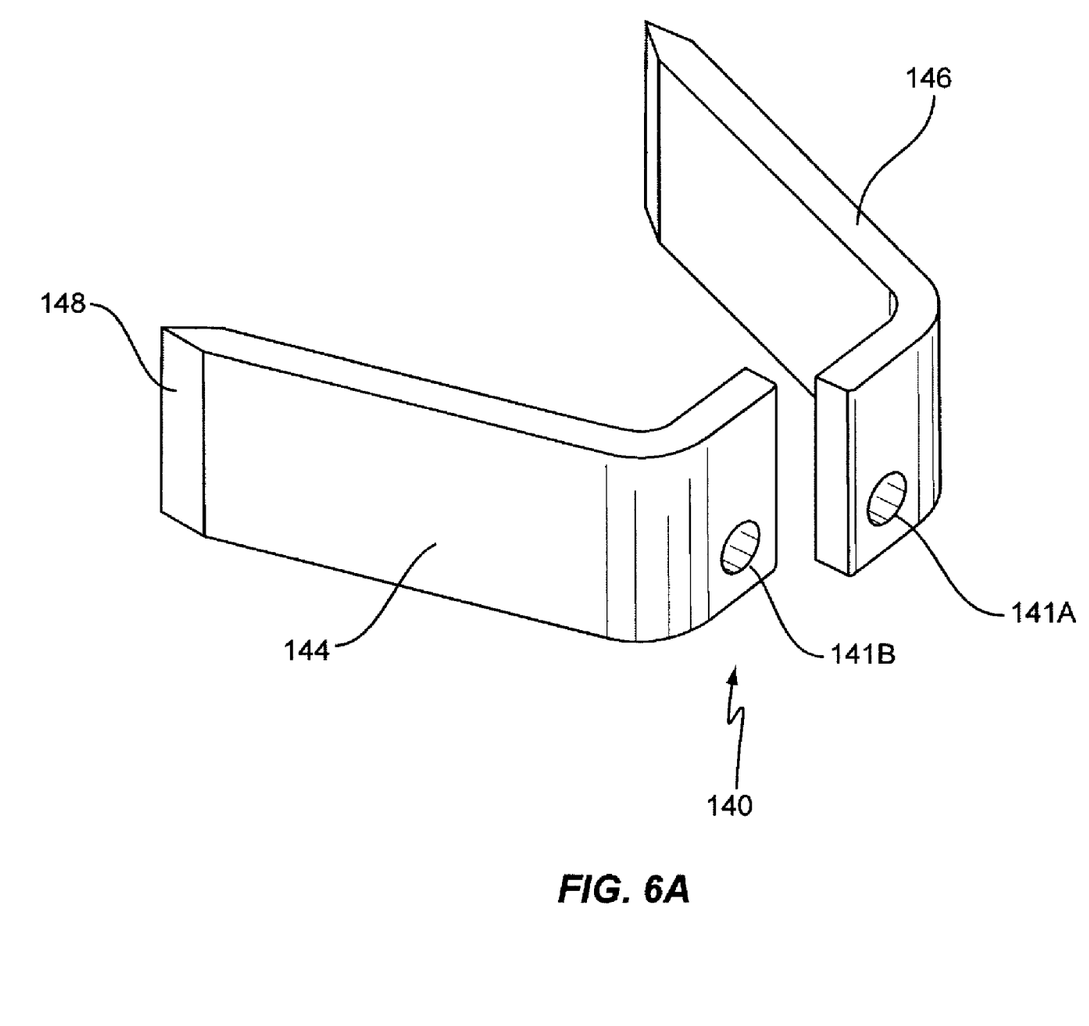
FIG. 6A shows the V-shaped staple that cooperates with the second embodiment of the spinal implant.

FIG. 6A shows the V-shaped staple 140 that cooperates with the second embodiment of the spinal implant 115. The V-shaped staple 140 comprises two halves or parts 144 and 146, instead of the two arms 44, and like V-shaped staple 40, each end 148 is pointed for penetrating the endplate of each vertebrae to which the plates 110 or 120 are being affixed.

Figure 6B:
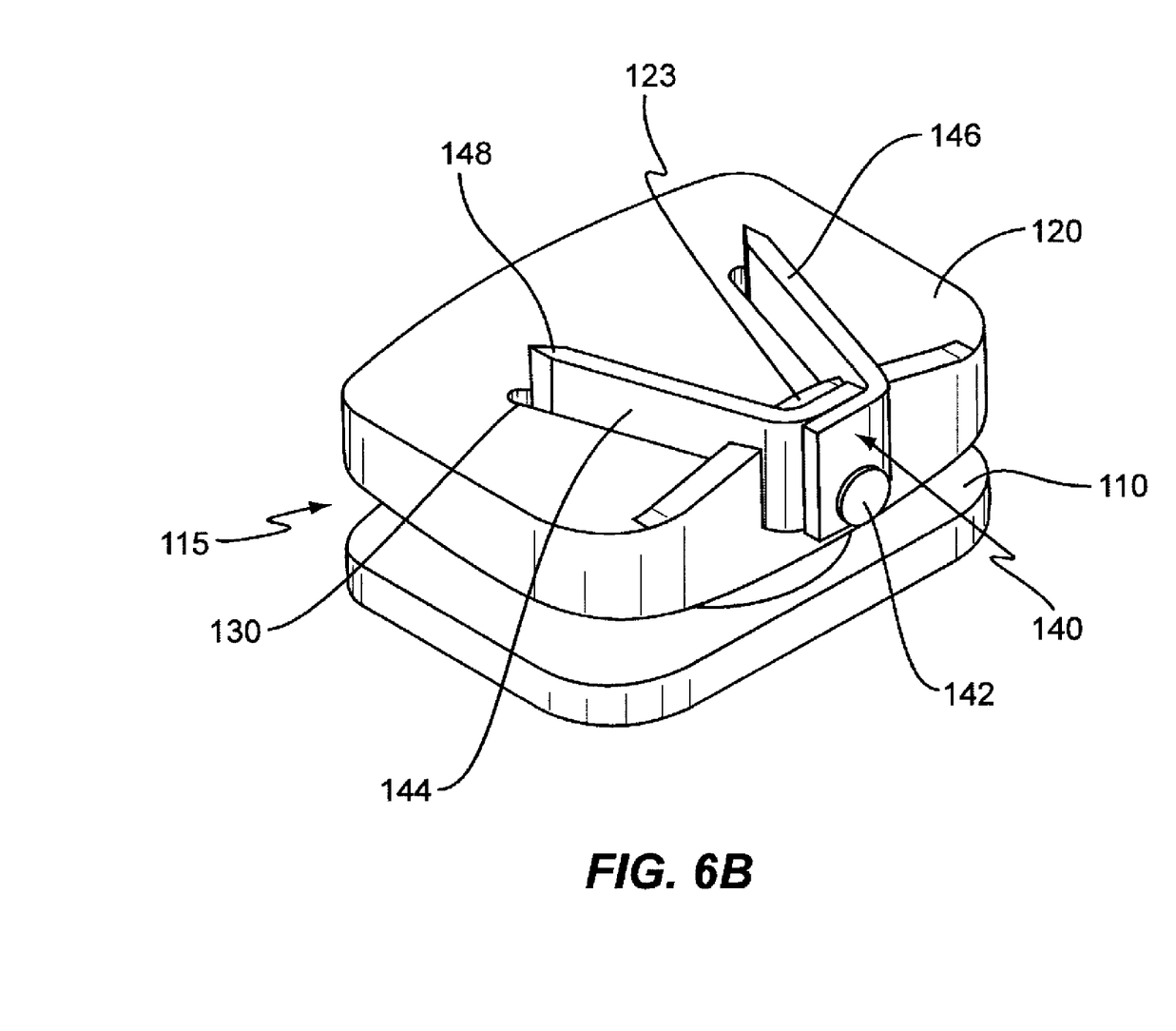
FIG. 6B shows the second embodiment of the V-shaped staple inserted in a spinal implant.

FIG. 6B shows V-shaped staple 140 already inserted in spinal implant 115. FIG. 6B also shows both the superior 120 and inferior 110 plates of the spinal implant 115, as well as the fastening screw 142 of the V-shaped staple 140. As compared to V-shaped staple 40, V-shaped staple 140 is shaped more like a "V" prior to use (as well as during use) from the start, and as shown in FIGS. 6A and 6B, V-shaped staple 140 can be stiffer than V-shaped staple 40 in that it does not need to bend to accommodate insertion in the grooves of the plates. The two parts or halves of V-shaped staple 140 allows one half 144 to be inserted, and then the next half 146 to be inserted thereafter, allowing for each part to be relatively rigid. Thus, the V-shaped staple 140 provides stability to the spinal implant, particularly transverse stability, while also preventing backing out of the implant in a relatively rigid manner.

Figures 7A, 7B, 7C:
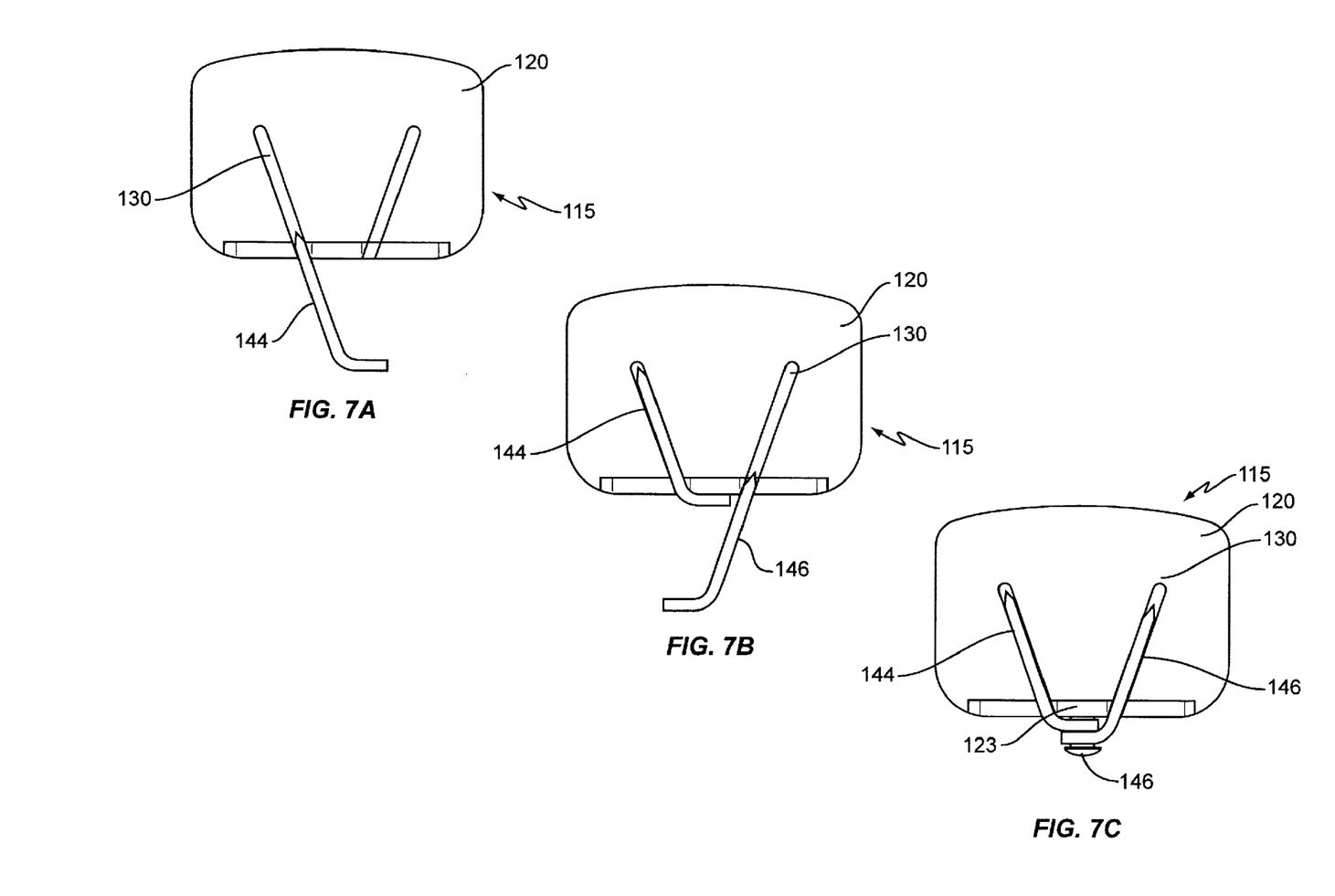
FIGS. 7A, 7B and 7C shows top views of the procedure for implanting the second embodiment of the V-shaped staple into the superior plate of the spinal implant of the present invention.

In top views, FIGS. 7A, 7B and 7C demonstrate the procedure, and specifically the beginning, middle and end stages, for implanting the V-shaped staple 140 into the superior plate 120 of the spinal implant 115 of the present invention. In FIG. 7A, the left half 144 of the V-shaped staple 140 is introduced to the implant 115 and the vertebra (not shown). The left half 144 of the V-shaped staple 140 can simply be hammered or power-driven through the vertebra that lies above the superior plate 20, while it moves through groove 130. In FIG. 7B, the right half 146 of the V-shaped staple 140 is introduced into the implant 115 and the vertebra, such that the holes 141A and 141B in each half (shown in FIG. 6A) line up over each other. The left half 146 of the V-shaped staple 140 can similarly be hammered or power-driven through the vertebra that lies above the superior plate 120, while it moves through groove 130. Then, as shown in FIG. 7C, when the halves 144 and 146 are fully in place, the fastening screw 142 can be inserted through holes 141A and 141B and into stop 123 to secure the V-shaped staple 140 to the implant 115. The same angle of the halves (or arms) 144 and 146 from center (or centerline) for the first embodiment of the present invention also is preferred for this second embodiment for achieving maximum stability to the spinal implant, particularly transverse stability, while also preventing backing out of the implant.

Figure 8:
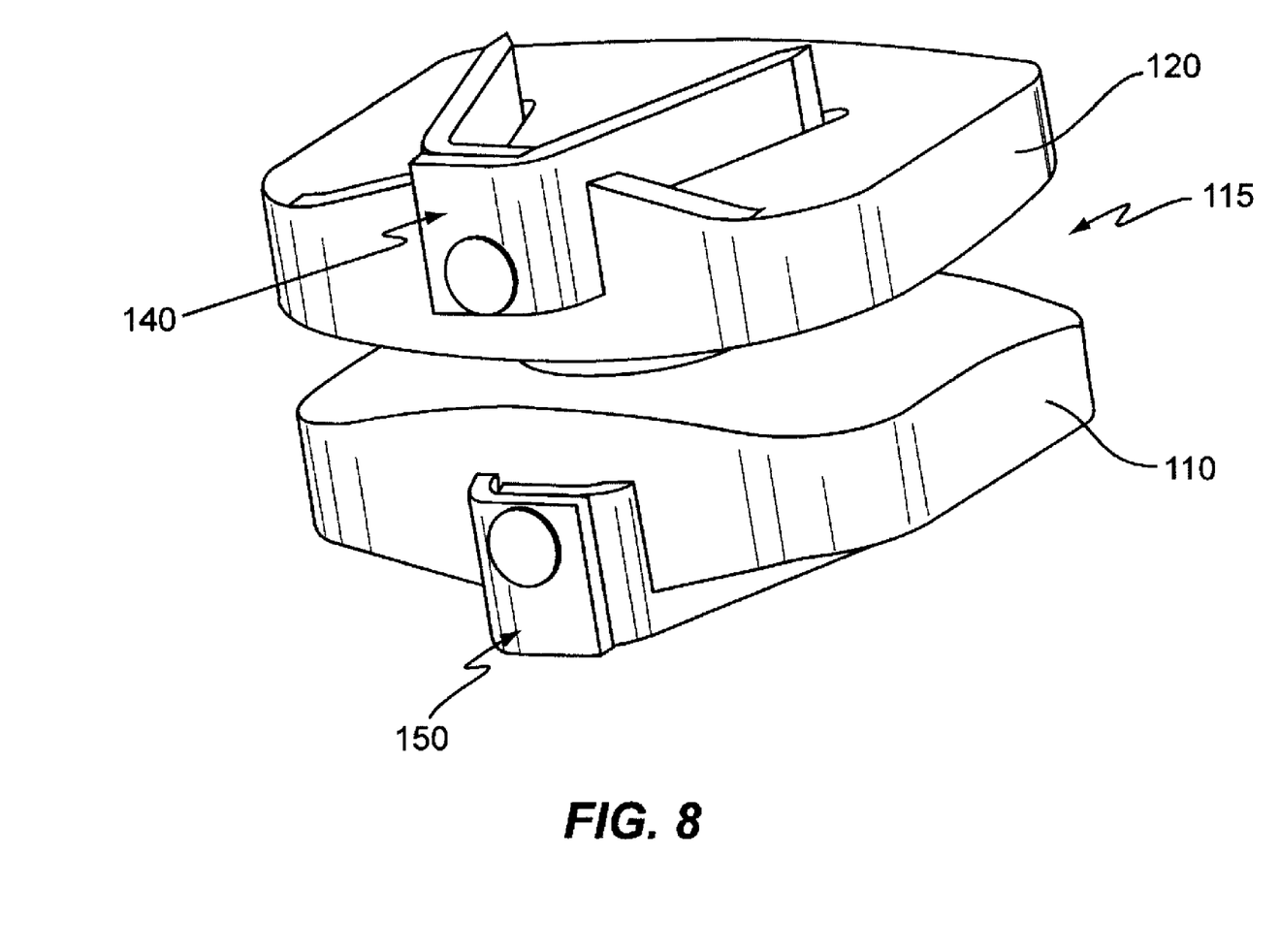
FIG. 8 shows the second embodiment of the V-shaped staple in cooperation with both the superior and inferior plates of an intervertebral disc.

FIG. 8 shows the second embodiment of the V-shaped staple 140 of the present invention in cooperation with both the superior and inferior plates 120 and 110, respectively, to achieve maximum stability and results, e.g., to prevent backing out. Specifically, a V-shaped staple 140 is shown in cooperation with a superior plate 120, and a V-shaped staple 150 is shown in cooperation with an inferior plate 110, where plates 120 and 110 are part of the same artificial disc 115.

A third embodiment of the present invention is illustrated and described with reference to FIGS. 3, 5, 9A, 9B, and 10. FIG. 3 shows the third embodiment of a V-shaped staple 240, while FIG. 5 depicts an artificial disc 115 that also can be used with V-shaped staple 240. Like the first two embodiments, the V-shaped staple 240 is made of the same materials, but typically is of a smaller thickness. Specifically, for the first and third embodiments of the V-shaped staple, the preferred range of thickness is in the range of 0.3 mm. to 1.0 mm. for metal materials, and 0.5 mm. to 3.0 mm. for non-metal materials. For the second embodiment, although it can be thinner than the other embodiments, the preferred range of thickness is in the range of 0.3 mm. to 3.0 mm. for all materials. Similarly, for the first and third embodiments of the V-shaped staple, the preferred range for angle α from the centerline CL is ½ degree to 15 degrees. For the second embodiment, however, the preferred range for angle α from the centerline CL is ½ degree to 65 degrees, and a more preferred range for α from the centerline CL is 10 degrees to 30 degrees.

Figure 9A:
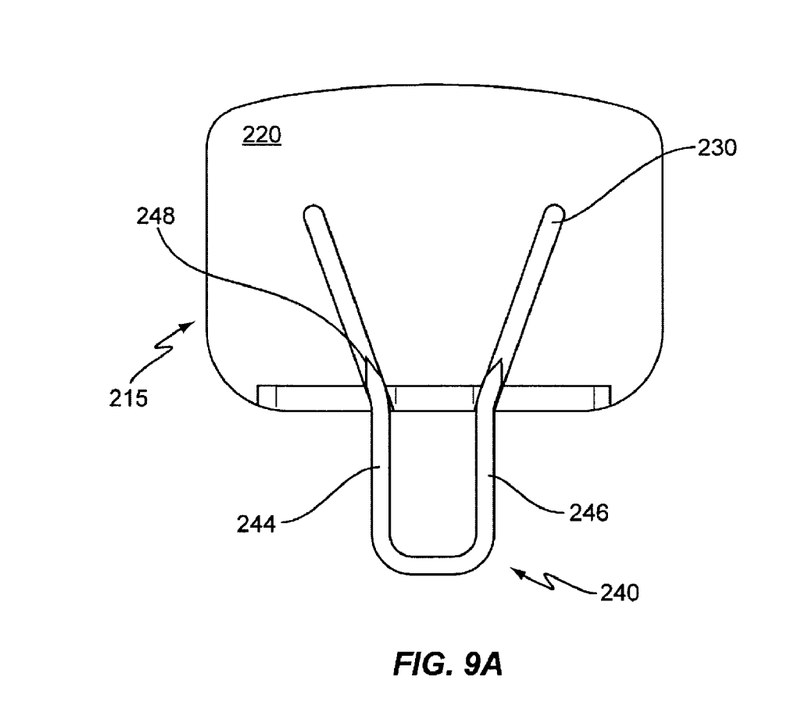
FIGS. 9A and 9B shows top views of the procedure for implanting the third embodiment of the V-shaped staple into the superior plate of the spinal implant of the present invention.
Figure 9B:
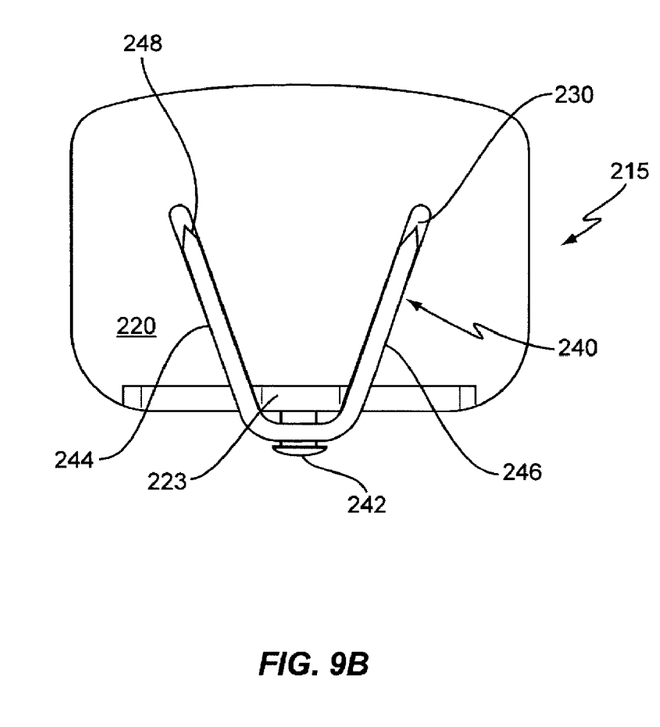

Accordingly, FIGS. 9A and 9B demonstrate the procedure, and specifically the beginning and end stages, for implanting the V-shaped staple 240 into the superior plate 220 of the spinal implant 215 of the present invention. In FIG. 9A, the V-shaped staple 240 is introduced into the implant 215 and the vertebra (not shown). With the aid of the pointed ends 248, the V-shaped staple 240 can simply be hammered or power-driven through the vertebra that lies above the superior plate 220, while it moves through groove 230. Because the staple 240 is relatively thin, it can yield to the angle of the groove 230 as it enters the implant 215, as shown in FIG. 9A. In FIG. 9B, when the V-shaped staple 240 is fully in place, the fastening screw 242 can be inserted through hole 41 and into stop 223 to secure the V-shaped staple 240 to the implant 215. The same angle of the halves 144 and 146 (or arms) from center for the first embodiment of the present invention also is preferred for this third embodiment for achieving maximum stability to the spinal implant, particularly transverse stability, while also preventing backing out of the implant.

Figure 10:
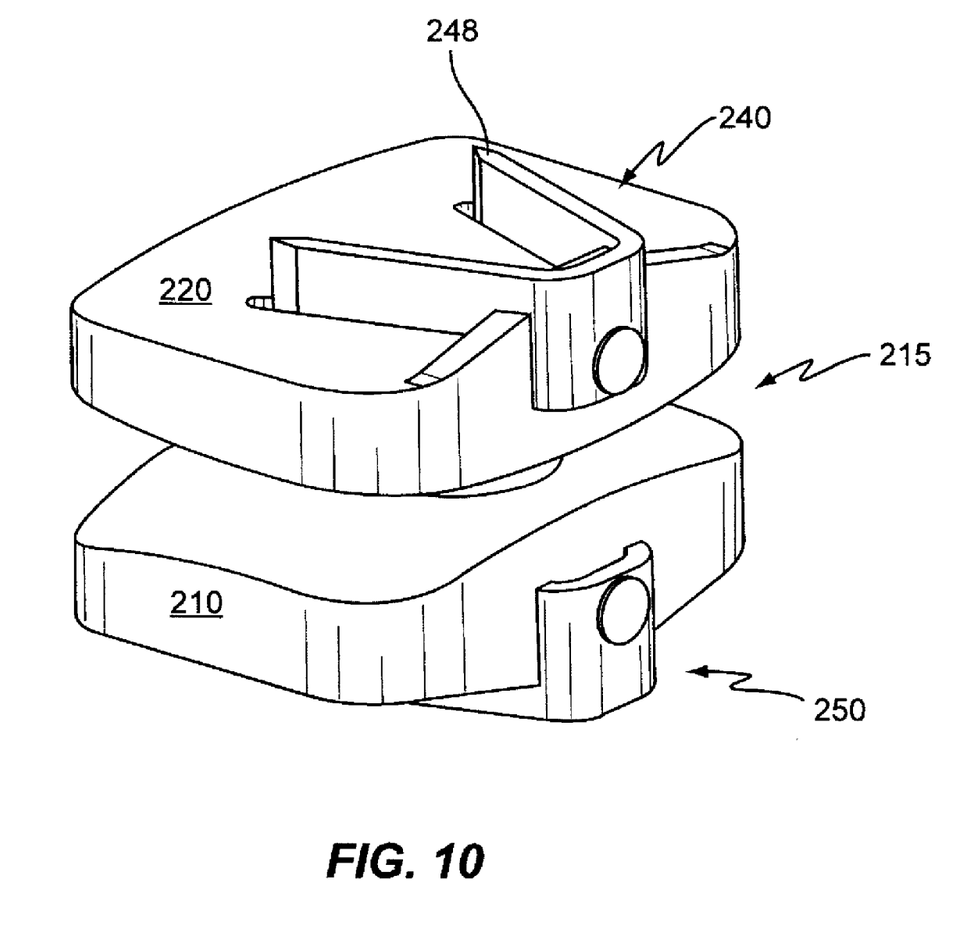
FIG. 10 shows the third embodiment of the V-shaped staple of the present invention in cooperation with both superior and inferior plates of an intervertebral disc.

FIG. 10 shows the third embodiment of the present invention V-shaped plate 240 in cooperation with both the superior and inferior plates 220 and 210, respectively, for maximum stability and results, e.g., to prevent backing out. Specifically, a V-shaped staple 240 is shown in cooperation with a superior plate 220, and a V-shaped staple 250 is shown in cooperation with an inferior plate 210, where plates 220 and 210 are part of the same artificial disc 215.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed:

1. An intervertebral implant system for positioning between an upper vertebra and a lower vertebra, the implant system comprising:
   an intervertebral implant comprising:
      an inferior plate and a superior plate, the superior plate having a vertebral surface facing the upper vertebra and the inferior plate having a vertebral surface facing the lower vertebra, each plate having an anterior portion and a superior portion wherein there are two grooves on at least one vertebral surface, each groove extending at an angle outward from a centerline on the vertebral surface as they extend from the anterior portion of the plate toward the posterior portion of the plate; and
      a staple to be associated with the two grooves when in use for maintaining stability of the intervertebral implant and preventing backing out of the intervertebral implant, the staple having two arms and having a generally rectangular shape prior to use, and when implanted, each arm extends at an angle outward from the centerline as each extends from the anterior portion of the plate toward the posterior portion of the plate.

2. The intervertebral implant system of claim 1, wherein an end of each arm of the staple is pointed.

3. The intervertebral implant system of claim 1, wherein the grooves are wider at the anterior portion of the plate than at the posterior portion of the plate.

4. The intervertebral implant system of claim 1, wherein the implant further comprises a stop situated on the anterior portion of at least one of the plates for helping the at least one plate maintain its proper position in the disc space.

5. The intervertebral implant system of claim 1, wherein the implant further comprises a screw for fastening the staple into the at least one plate to which the staple is inserted.

6. The intervertebral implant system of claim 1, wherein the implant further comprises a second staple for fastening the staple into the other of the superior or inferior plate such that both the superior and inferior plates each have a single staple helping to maintain stability of the intervertebral implant and to prevent backing out of the intervertebral implant.

7. The intervertebral implant system of claim 1, wherein the implant system is motion preserving.

8. The intervertebral implant system of claim 1, wherein each arm of the staple has a thickness in the range between 0.3 mm. and 3.0 mm.

9. The intervertebral implant system of claim 1, wherein the two grooves on the at least one vertebral surface extend at an angle outward from the centerline on the vertebral surface in the range of 0.5 degree to 15 degrees from the anterior portion of the plate toward the posterior portion of the plate.

10. An intervertebral implant system for positioning between an upper vertebra and a lower vertebra, the implant system comprising:
an intervertebral implant comprising:
an inferior plate and a superior plate, the superior plate having a vertebral surface facing the upper vertebra and the inferior plate having a vertebral surface facing the lower vertebra, each plate having an anterior portion and a superior portion wherein there are two grooves on each vertebral surface, each groove extending at an angle outward from a centerline on the vertebral surface as they extend from the anterior portion of the plate toward the posterior portion of the plate; and
two staples to be associated with the grooves when in use, one on each vertebral surface for maintaining stability of the intervertebral implant and preventing backing out of the intervertebral implant, each staple having two arms and having a generally rectangular shape prior to use, and when implanted, each arm of each staple extends at an angle outward from the centerline as each extends from the anterior portion of the plate toward the posterior portion of the plate.

11. The intervertebral implant system of claim 10, wherein an end of each arm of each staple is pointed.

12. The intervertebral implant system of claim 10, wherein the implant further comprises stops situated on the anterior portion of each plate for helping each plate maintain its proper position in each respective vertebra.

13. The intervertebral implant system of claim 10, wherein the implant further comprises two screws, one each for fastening each staple into each plate to which each staple is inserted.

14. The intervertebral implant system of claim 10, wherein the two grooves on the at least one vertebral surface extend at an angle outward from the centerline on the vertebral surface in the range of 0.5 degree to 15 degrees from the anterior portion of the plate toward the posterior portion of the plate.

15. An intervertebral implant system for positioning between an upper vertebra and a lower vertebra, the implant system comprising:
an intervertebral implant comprising:
an inferior plate and a superior plate, the superior plate having a vertebral surface facing the upper vertebra and the inferior plate having a vertebral surface facing the lower vertebra, each plate having an anterior portion and a superior portion wherein there are two grooves on at least one vertebral surface, each groove extending at an angle outward from a centerline on the vertebral surface as they extend from the anterior portion of the plate toward the posterior portion of the plate; and
a staple to be associated with the two grooves when in use for maintaining stability of the intervertebral implant and preventing backing out of the intervertebral implant, the staple consisting essentially of a left half and a right half, each half extending at an angle outward from the centerline as each extends from the anterior portion of the plate toward the posterior portion of the plate.

16. The intervertebral implant system of claim 15, wherein an end of each arm of the staple is pointed.

17. The intervertebral implant system of claim 15, wherein the implant further comprises a stop situated on the anterior portion of at least one of the plates for helping the staple maintain its proper position in the disc space.

18. The intervertebral implant system of claim 15, wherein the implant further comprises a screw for fastening the staple into the at least one plate to which the staple is inserted.

19. The intervertebral implant system of claim 15, wherein the implant further comprises a second staple for fastening the staple into the other of the superior or inferior plate such that both the superior and inferior plates each have a single staple helping to maintain stability of the intervertebral implant and to prevent backing out of the intervertebral implant.

20. The intervertebral implant system of claim 15, wherein the two grooves on the at least one vertebral surface extend at an angle outward from the centerline on the vertebral surface in the range of 0.5 degree to 65 degrees from the anterior portion of the plate toward the posterior portion of the plate.

* * * * *